United States Patent [19]
O'Bryan et al.

[11] Patent Number: 5,966,309
[45] Date of Patent: Oct. 12, 1999

[54] CLINICALLY TESTING BIOLOGICAL SAMPLES

[75] Inventors: David P. O'Bryan, Kennett Square, Pa.; Kevin N. Constable, Claymont, Del.; Peter Sagona, Collegeville; Bingham H. Van Dyke, Jr., Gilbertsville, both of Pa.

[73] Assignee: SmithKline Beecham Corporation, Philadelphia, Pa.

[21] Appl. No.: 08/827,212

[22] Filed: Mar. 28, 1997

Related U.S. Application Data

[63] Continuation of application No. 08/390,463, Feb. 16, 1995, Pat. No. 5,623,415.

[51] Int. Cl.$^6$ ............................................. G06F 19/00
[52] U.S. Cl. ..................... 364/478.13; 198/617; 422/65
[58] Field of Search ..................... 364/478.13, 478.16, 364/478.17, 478.18; 198/349.6, 781.01, 617; 422/63, 65, 67

[56] References Cited

U.S. PATENT DOCUMENTS

| | | | |
|---|---|---|---|
| 4,325,910 | 4/1982 | Jordan | 422/64 |
| 4,707,251 | 11/1987 | Jenkins et al. | 209/569 |
| 5,038,911 | 8/1991 | Doane et al. | 198/357 |
| 5,087,423 | 2/1992 | Ishibashi | 422/67 |
| 5,191,967 | 3/1993 | Woltjer et al. | 198/781 |
| 5,208,762 | 5/1993 | Charhut | 364/478 |
| 5,315,094 | 5/1994 | Lisy | 235/385 |
| 5,324,025 | 6/1994 | Chadwick | 271/306 |
| 5,348,705 | 9/1994 | Koreyasu et al. | 422/67 |
| 5,351,801 | 10/1994 | Markin et al. | 198/346.1 |
| 5,623,415 | 4/1997 | O'Bryan et al. | 364/478.13 |

*Primary Examiner*—Paul P. Gordon
*Attorney, Agent, or Firm*—James M Kanagy; Charles M Kinzig

[57] ABSTRACT

This invention relates to an automated apparatus for subjecting samples to one or more selected test procedures at one or more test stations comprising a conveyor line for transporting samples contained in uniquely labeled containers, said line having at least two lanes for routing said containers to one or more selectable test stations, at least one of said lanes being a transport lane and at least one of said lanes being a queue line, and having a container interface device for transferring containers to said testing device from the queue lane and back again onto said queue lane.

15 Claims, 3 Drawing Sheets

CLINICALLY TESTING BIOLOGICAL SAMPLES

This is a continuation of application Ser. No. 08/390,463, now U.S. Pat. No. 5,623,415 filed Feb. 16, 1995.

SCOPE OF THE INVENTION

This invention relates to an automated apparatus for subjecting samples to tests, particularly for subjecting biological samples to clinical tests. The invention also relates to an automated process using the apparatus.

BACKGROUND OF THE INVENTION

Automated apparatus for subjecting samples, for example biological samples such as blood, urine, saliva, cerebrospinal fluid and other biological materials to one or more of a series of selectable clinical tests such as hematological tests, urinalysis, immunoassay, toxicology or other specific chemical tests, is known. In general such automated apparatus for clinical tests is constructed to test samples of biological materials which are obtained by a tester, such as a doctor or clinician, from a test subject, and which are sent for testing contained in tubes which are labeled to enable them to be associated with the originating test subject. Such automated apparatus generally comprises a conveyor line for transporting the samples in containers such as tubes to selected test stations at which tests are carried out, usually by presenting the sample in the tube, or a withdrawn specimen of the sample to test equipment. Test equipment of this type which is adapted to be used in combination with such a conveyor line is well known in the art. At each test station test result data is recorded and associated, usually by electronic data processing equipment, with the identity of the sample, thereby enabling this test result data to be related to the test subject from whom they originated.

There is a need for such automated testing apparatus to process samples at a high rate, so as for example to provide the tester, and ultimately the originating subject, with the results of the tests as quickly as possible. However it is also essential that the achievement of a high processing rate in such apparatus does not sacrifice accuracy of testing and reliable correlation of test result data with the identity of the sample.

It is an object of this invention to provide an automated apparatus for subjecting samples, particularly biological samples to tests, which increases the rate of processing of samples while maintaining such accuracy and reliability. Other objects and advantages of the present invention will be apparent from the following description.

SUMMARY OF THE INVENTION

This invention relates to an automated apparatus for subjecting samples to one or more selected test procedures at respective test stations, said apparatus comprising;
 a first conveyor line for transporting samples contained in uniquely labeled containers, said line having at least two lanes with means for routing containers between said lanes, at least one lane being a transport lane and at least one other lane being an accumulator lane,
 loading means for loading said containers onto the apparatus,
 electronic means for reading and recording the unique label information from said labels of containers,
 data processing means for electronically recording, storing and processing said information,
 electronic control means for routing and tracking said samples in response to said recorded information,
 at least one interface means for routing containers from the first conveyor line to a spur conveyor line,
 one or more spur conveyor lines for transporting said containers to one or more selectable test stations, said spur line(s) having at least two lanes, with means for routing containers between said lanes, at least one of said lanes being a transport lane and at least one of said lanes being a queue lanes and having a container interface device and a sample testing procedure located adjacent to said spur line(s),
 selection means and routing means, controlled by said data processing means, for selecting containers for routing by the interface device from the first conveyor transport lane to the transport lane of a selected spur line,
 selection means and routing means, controlled by said data processing means, for selecting containers and for routing selected containers from the spur transport lane to the queue lane adjacent to a selected test station,
 a container interface device for presenting a container or sample from the container to a test procedure and capable of interacting with a container in the queue lane and the staging area of a test procedure,
 test means for carrying out the test procedure,
 means to record and store the results of the said test procedure,
 means to route containers from the queue lane to the spur line transport lane,
 at least one interface means for routing containers from the spur conveyor line to the first conveyor line, and
 off-loading means to off-load containers from the apparatus.

GENERAL DESCRIPTION OF THE INVENTION

DESCRIPTION OF THE INVENTION

This apparatus is particularly suitable for subjecting samples of biological materials to clinical test procedures for example of the general types discussed above and may be used in conjunction with known automated test equipment of the type discussed above, which may be floor or table mounted, for example on adjustable height tables to enable ease of integration with the apparatus. Also the apparatus of the invention is suitable for use with clinical tests which require some manual procedures, e.g. transfer to a long term incubation procedure, and the term "test station" used herein refers to parts of the apparatus where containers are presented either for automated or tests requiring manual procedures.

Samples of biological materials may be contained in tubes such as those having conventional rubber bung closures or screw cap closures of a generally known type commonly used in the art of clinical testing. As is normal practice in the art of clinical testing samples of biological materials are obtained at a sampling site by a sampler or under the sampler's supervision from the test subject by an appropriate sampling procedure, and are then introduced into a container such as a tube by the sampler or under the sampler's supervision. The tube is then normally uniquely labeled by the sampler or under the sampler's supervision at least with information relating to the identity of the test subject and sent, together with test requisition documentation identifying the test(s) to be carried out, to a receipt area of the testing site where the apparatus of the invention is located. Alternative forms of containers for biological samples include slides, absorbent strips or pads etc. impregnated with a liquid or solid sample for testing. However the sample is contained in the apparatus of this invention, the sample may be subjected to standard known preservative or pre-treatment steps before subjecting to the tests.

The unique labeling applied to the tube for the apparatus of this invention may for example be the unique labeling applied at the sampling site as mentioned above, or may for example be unique labeling subsequently applied to the tube and based upon the unique labeling and/or test requisition documentation accompanying the tube to the testing site. The unique labeling is preferably machine-readable labeling, for example optically readable bar-codes of a generally known type, which is preferred, or alternately magnetic strips or optically readable characters etc. The unique labeling suitably encodes at least information relating to the identity of the container, i.e. enabling the container to be associated with the test subject, and information relating to the tests to which the sample contained therein is to be subjected. The unique labeling may comprise an adhesive label manually or mechanically affixed to the tube, or may comprise other forms of labeling such as for example direct printing upon the tube wall. Labels should be placed on or in the container in such as way as to be readable during processing.

When the containers are tubes of the above-described type they are mounted during transport on the first and spur conveyor lines in holders. This is desirable as tubes are generally in the form of glass or plastics materials tubes which require a stable mounting for safe transport on the conveyor lines of the apparatus to minimize risk of for example falling over on the line. Such holders may be made of plastics materials and may include a resilient-sided gripping cavity in which the tubes may be gripped while oriented upright. Such holders have a heavy, e.g. metal, base to lower the center of gravity of the tube-holder combination and thereby to impart stability against falling. The holders may incorporate guide means engageable with part of the conveyor line, e.g. one or more grooves engageable with a guide rail adjacent to the conveyor line, to assist in safe transport of the holder along the conveyor line. It is also preferred that the combination of holder and tube, or the tube within the holder, is capable of rotation about an axis perpendicular to the conveyor line for example by means of engagement with part of the conveyor or with a rotating mechanism of the conveyor, so as to enable the unique labeling to be presented to the means for reading information regardless of the position and/or orientation of the label on the container.

If the containers are the above-described slides, pads or strips, holders of a type suitable for these and including the above mentioned suitable and preferred features appropriate to such containers may be used.

The first conveyor line may be linear, i.e. returning to its starting point without being able to transport samples back to the starting point, or circulating. It is preferred to use a circulating conveyor line which can circulate samples thereon back to the starting point.

The first conveyor line may be a substantially flat conveyor belt (optionally with alpine sections) of flexible links thereby allowing linear and circulating operation in substantially a flat plane. An example is a layout including antiparallel moving linear straight sections. Flat belts of this type are known in the art, for example a known Flex-Link XM™ series conveyor with a horizontal variable speed drive, operable between for example speeds of 10–50 fpm, e.g. 10–30 fpm.

Preferably there is a single first conveyor line, although two or more first conveyor lines may be operated in series or in parallel to enlarge the handling capacity or processing speed of the apparatus. The said lanes of the first conveyor may be provided by utilizing a single broad conveyor belt and subdividing the belt across its width into respective lanes. Such subdivision may be by means of edge walls defining the outer edges of the lanes and one or more dividing walls located at intermediate positions between the edge walls, and dividing a single conveyor belt into the required number of lanes. The edge walls and dividing walls may comprise the above-mentioned guide rails.

As regards the two basic lanes in the first conveyor line, the function of the transfer lane is to move containers around the apparatus and the function of the accumulator lane is to move containers into position to be acted on or to be warehoused pending available space on a destination spur or the like. Once the container has been acted on in the accumulator lane it is routed back to the transfer lane. Preferably the selection means and an active routing means will be located solely on the transfer lane, and all devices, testing modules, and off-loading means will be located on the accumulator lane. Preferably the transport lane will be on the inside and the accumulator lane will be on the outside of an apparatus which has a circulating conveyor line design.

The function of the first conveyor line transport lane is inter alai to transfer containers to a destination such as a remote point where they are routed to the accumulator line for action or to a spur line. This lane transports the containers around the first conveyor line to a selection means and routing means at which point the containers are transferred to either the accumulator lane or a spur line. Furthermore, this transport lane receives the containers back from the accumulator lane or a spur line via the return means and transports the containers to another destination such as the off-loading means. A preferred embodiment will locate the transfer lane on the inside of the circulating line comprising the first conveyor line. This lane will preferably have active selection means and active transfer means such as movable gates for selecting and routing containers to the accumulator lane or a spur utilizing the information gleaned from the unique information on the container label.

The function of the accumulator lane is inter alai to provide a siding to which containers can be shunted for being acted on in some fashion after which they are returned to the transfer lane by a passive merge device (said return means). This lane also serves as an accumulation area where containers can be held in anticipation of being routed to a selected destination which is currently unavailable.

As regards the way in which containers are routed between transport and accumulator lane, the transport lane may be provided with selection means and routing means controlled by the data processor for selecting containers and for routing selected containers from the transport lane to the accumulator lane. The accumulator lane may also be provided with selection means and routing means controlled by said data processor for selecting containers and for routing selected containers from the first conveyor accumulator lane to the transport lane, but the preferred operation is to use a stop which holds the containers on the accumulator lane for a period, then releases them to a passive merge gate which directs them back to the transport lane.

The first conveyor may have a single accumulator lane serving these functions. Alternatively there may be more than one accumulator lane, for example a second accumulator lane for storage of containers or for gathering of containers into groups of two or more containers for transport to testing stations for which testing is advantageously carried out upon such groups of containers.

The loading means may be manual or wholly or partly automated. The loading means preferably loads the containers onto the accumulator lane of the first conveyor line. The loading means may load containers directly onto the first conveyor line. Alternatively the loading means may, load the containers onto a loading spur conveyor line from which they are routed to the first conveyor line. Alternatively the loading means may load the containers onto one first conveyor line from which they are transferred to another first conveyor line. Manual loading of containers onto the first conveyor line may be by means of depositing the labeled containers which have been placed in holders onto the first conveyor line by hand An automated loading means may comprise a conveyor upon which labeled containers are deposited, e.g. by hand, having guiding means such as a tapering region to direct deposited containers into a sequential stream of single containers, and feeding means to feed this stream sequentially onto the first conveyor. The feeding means may comprise a known gate means such as a stepwise rotating wheel having circumferential receptacles each for a single container, by means of which a single container may be received into a receptacle from the stream, then by stepwise rotation be transferred onto the first conveyor with a suitable interval between containers. Alternative automated loading means will be apparent to those skilled in the art.

When containers are loaded onto the apparatus it is preferred to have done a prior check to insure that the label is readable and in a readable position if placed in a carrier device such as a puck. Once the containers are loaded onto the accumulator lane they are routed to the transfer lane where a second check may be performed to insure that the label is being properly read by the apparatus' automated reading devices, if they are being used. Preferably this review will comprise the first station on the transfer lane.

The means for reading and recording information from the labels may comprise known reading means appropriate to the nature of the label. For example one may use an optical bar code reader, a magnetic head or an optical character reader. Bar coding is preferred. It is preferred that the whole process of reading and acting on the container can take place within 0.5 sec. Preferably an initial means for reading and recording information are located at the point where the containers are loaded onto the first conveyor in which case the means may be at or comprise a part of the loading means, or may be adjacent to the first conveyor at a position downstream of loading the containers onto the first conveyor. The function of such initial means is to identify and record information about the containers relating to the identity of the patient, type of sample and the test to be done on that sample. This is in effect "checking in" the samples so that they can be tracked and routed through the apparatus.

The means for reading information at a particular point may include stopping means for temporarily stopping the movement along the conveyor of individual containers of which the label is to be read along the container so that the label may be held for a suitable length of time in the reading field of a reading means. Such stopping means suitably comprise sensors such as photoelectric or capacitance sensors which detect the presence of a container, and singulator means to isolate and stop a single container on the conveyor in the reading field. Singulator means may be of a known type, and may for example comprise moveable barriers which move in response to detection of a container by the sensor, so that a single container is isolated between two barriers. The means for reading information may include means for orienting the container relative to the reading field of the reading means so the label can be read. Such rotating means may be the above-described engagement of rotatable holders with the conveyor. Constructions of such stopping and rotating means will be apparent to those skilled in the art. Alternatively a second reader can be placed on the opposite side of the lane to provide two read-outs thus avoiding the need to rotate the carrier.

The recording and data processing means may be a computer or microprocessor programmed with appropriate software of a nature apparent to those skilled in the art. The data processing means must have sufficient computational and storage capacity to handle the real time control of the apparatus and to process data from the apparatus if that function is accorded to a single device. Apparatus control functions and data management functions can be done by the same computational device, or by separate devices. A preferred embodiment is to have a controller for the lines, the selection and routing means and a primary data processor which has an interface with this controller. A most preferred embodiment is one in which the controller and the data processor are bidirectional, that is the controller communicates with the data processor and the data processor in turn communicates with the controller. Normally the data processor will control the container interface device and the test module and receive output from the test module. This has been called a process control management execution system (PC/MES). An example of a controller is the Allen Bradley PLC 5/40E™. One or more of any of the commercially available computers can be used to carry out the PC/MES function.

The spur conveyor line comprises a substantially flat conveyor belt (optionally with an alpine section) flat belt of flexible links thereby allowing operation in substantially a flat plane, for example in a layout including antiparallel moving linear straight sections. Flat belts of this type are known in the art, for example a known Flex-Link XM™ series conveyor with a concatenated variable speed drive, suitably between 10–50 fpm, e.g. 10–30 fpm. While a spur may be a simple out-and-back line, it may be preferable to have a means for recycling containers back through the line without routing them off to the first conveyor line. This is particularly useful in the event the queue lane (described below) can not accept a container for some reason and rather than recycle the container the whole way back out onto the first line, then back on the spur, the container can simply be cycled repeated around the spur until the queue lane for its designated test can accept it.

There may be one or more spur lines. The number of spur lines is determined inter alai by the size of the test equipment at the test stations and/or the handling capacity or processing speed of the apparatus. For example the same test can be carried out on two or more spur lines to increase capacity or to provide a back-up.

A spur line will have at least one transport lane and at least one queue lane. Said lanes of the spur conveyor may be of a construction similar to that of the first conveyor line. The lanes may be defined by edge walls defining the outer edges of the lanes and one or more dividing walls located at intermediate positions between the edge walls, and dividing a single conveyor belt across its width into the required number of lanes. The edge walls and dividing walls may comprise the above-mentioned guide rails.

The function of the spur's transport lane(s) is inter alai to move containers around the spur thus providing a means for routing them to a preselected testing station. Each spur conveyor line may have one or more transport lanes. The transport lane of the spur line also acts as a bypass lane along which containers may travel and bypass the test station(s) if they are not selected for testing. The transport lane may be either the inner or the outer lane; preferably it will be the inside lane of a circulating line. The transport lane will preferably have on it the selecting means and the routing means for routing containers into the queue lane.

The function of the queue lane of the spur conveyor line is similar to that of the accumulator lane in the first conveyor line in that is provides an area where the container can be acted on by the interface device and/or the testing module set up adjacent to the spur line. Thus containers in the queue lane are presented to the interface device for that test procedure while minimizing interference with the movement of containers along the spur line transport lane.

The spur transport lane preferably will be a circulating lane; the queue lane need not be so. This may be achieved by providing a circulating lane linking a part of the spur transport lane upstream of the point where the containers are returned from the spur line to the first conveyor line to a part of the spur conveyor downstream of the point where the containers are routed to the spur line from the first conveyor line, and selection means and routing means, controlled by said data processing means, for selecting containers and for routing selected containers from the spur conveyor line transport lane to the said circulating lane. The circulating lane may be a conveyor belt of similar construction to the spur conveyor line or the first conveyor line, for example a Flex-Link XM or XS™ style conveyor or an alternative such as a rotary carousel.

While any number of test stations can be placed on the periphery of a spur, it is expected that a three meter section of spur will have two test stations on either side. This number is not critical to the practice of the invention but represents a practical placement of machines and devices.

Electrical, air, water, communication means and the like can be slung under the superstructure of the spur so they are out of the way but yet are readily accessible when needing repair. Preferably spurs will be set up as a module which can be treated as a plug-and-play system. This approach may also have electronic controllers build into the underbelly of the spur in close proximity to the selection means and routing means they control.

The container interface device is a device which can engage the container and/or a holder in which a container is mounted and present either to a test procedure staging area or to a test device sampling mechanism. Another embodiment is one in which this device removes a specimen of the sample directly from the container and places it in the receptacle of a test device sampling mechanism. In the simplest embodiment, a person may remove containers from the queue lane and place them in the staging area of a given test procedure.

Container interface devices which can perform these functions are known, or known devices can be modified for use in the apparatus of the invention. Examples of such interface devices include the following. A direct sampling engine, for example in which a container is moved from the queue lane to the sampling port of a test equipment. A pick-and-place engine, with a robot arm and grip, moving and operating responsive to container sensors, which can pick a container or a holder plus container from the queue lane and present the container to test equipment adjacent to the queue lane, for example placing the container in a feed magazine such as a carousel of test equipment. The pick-and-place engine will have at least one grip which can pick a container to be tested from the queue lane. Preferably two or more grips will be used. This allows for addressing multiple containers at one time. For example with two grips, one grip can remove a tested container from the test equipment while the other is removing another tube from the conveyor line. Another useful interface device is a pipetting engine which can insert one or more pipette tips into respective one or more containers to withdraw specimens of the samples for testing therefrom and present the withdrawn specimens to the test equipment. A batch movement engine which can remove numbers of containers from the queue line and load them into recorded positions in racks is yet another example of a useful interface device. The human hand can also be used.

It is preferred that before or during interface of the interface means with the container, means for reading and recording information from the labels of the containers which may be of similar construction to the reading and recording means discussed above, is used inter alai to read information from the label and via the data processing means correlate the identity of the container with the identity of a container recorded by the initial means for reading and recording information, and to correlate a specific test result with the identity of a sample being tested.

The test procedure comprises a test appropriate to the sample. For example in the case of biological samples this can be the clinical tests discussed above. These tests can be done using automated test equipment as discussed above. Alternately testing procedures may submit to manual processing.

As regards the selection means used in this invention, those means may comprise means for reading and recording information from the label on the container, e.g. as described above. The information read from the label suitable includes at least information relating to the identity of the container, which may be correlated with the identity of a container recorded by the initial means for reading and recording information, and information relating to the nature of the tests, so that the data processing means can confirm the identity of the container, and select whether to route containers to a spur line from the first conveyor line which transports the container to an appropriate test station, or from a spur transport lane to a queue lane adjacent to an appropriate test station. Additionally or alternatively the selection means may identify defects in the container, of the nature discussed above, and route containers to an accumulator lane.

The means for routing selected containers from the first conveyor transport lane to the transport lane of a selected spur line, for routing selected containers from the spur transport lane to the queue lane adjacent to a selected test station, for routing containers from the queue lane to the spur transport lane, for routing selected containers from the first conveyor transport lane to the accumulator lane, and for routing selected containers from the first conveyor accumulator lane to the transport lane may comprise singulator means to isolate a single container on the conveyor and a divertor means to divert the isolated container from one said lane to another, at a place where the two said lanes run adjacent and in parallel motion.

Divertor means may comprise fixed (passive) or moveable (active) barriers acting in response to a signal and which can move between a position which allows unobstructed travel along one lane but blocks access to another lane, and a position which blocks access to the first mentioned lane but diverts containers along the second mentioned lane. Fixed divertors are within the skill of the art. Ways of constructing movable barriers will also be apparent to those skilled in the art. It has been found that moveable barriers which move at a suitable speed are pivoted swinging barriers in which the movement is caused by compressed air actuation, the air supply being controlled by solenoid valves responsive to the data processing system.

As regards the interface device for transferring containers from the first conveyor line to the spur conveyor line, it may comprise a transfer conveyor onto which the divertor means may route containers from the first line transport lane and thus into the transfer lane of the spur line. The interface device may anything which is capable of transferring the containers from the first line to the spur. Manual means can be used. It is preferred to place both lines immediately adjacent to each other on the same level and use a mechanical device which can move the containers from one belt to the other without interrupting the normal movement of the containers. A preferred example is to use a single lane Flex-Link XS™ style conveyor belts running side by side with a set guide rail which routes prior selected containers of the first line to the selected spur's conveyor belt. Alternative routing means will be apparent to those skilled in the art, such as motor driven turntables, or turntables driven by the conveyor line.

Test data may be output and stored by any known means. Data can be manually outputted, stored in the test device, or electronically off-loaded to a computational device. The means to electronically record and store the results of the said testing procedures may comprise a data processing system such as a computer or microprocessor. This may be the same data processing system that records the said information from labels, but the invention is not so limited.

The means for routing containers from the transfer lane of the spur line to the first conveyor line comprises the same functionality as was described above for routing containers from the first conveyor line to a spur line. It is preferred to use the same mechanism for this return routing as is used for routing a container to a spur, but that is not mandatory for the practice of this invention.

An off-loading means is utilized to remove fully tested containers from the apparatus. This off-loading can be done at any time or at any point on the apparatus. Preferably the containers will be directed, back to the first conveyor line where they will then be removed from the apparatus. However, containers may be off-loaded from a spur line if so desired. Containers may be directed to the part of the apparatus which has the off-loading means. This can be done by a set divertor or by a selection and routing means of the type discussed above.

The off-loading means will remove the containers from the line or from a holder or other carrier device which was used to transport the container around the apparatus. This is achieved by manual or mechanical means. For example tubes can be manually pulled from the holders and placed in some repository such as a trash can or an indexed box for storage. Mechanical devices can be used for this task. For example a pick-and-place robot can be used to pull tubes from holders and place them in a receptacle. A preferred off-loading means is a pick-and-place robot which deposits tubes in recorded mapped locations recorded in the data processing system so that the identity of the tubes may be retrieved for re-testing.

The first conveyor line and spur line may each be driven by a motor such as an electric motor of known type specific thereto, or a single motor may drive both the first conveyor line and the spur conveyor. A dedicated motor can drive the circulating conveyor line.

The first conveyor line or a spur conveyor line may also include a decapping means to remove bungs or caps from containers such as tubes if this is necessary for the testing procedure. The first conveyor line or a spur conveyor line may also include a re-capping means to apply a closure over the mouth of open or decapped containers such as tubes, at a stage in the operation of the apparatus when presentation of open or decapped containers to any testing procedures requiring decapped containers has been carried out.

The apparatus of the invention suitably incorporates other desirable features as summarized below.

SPECIFIC PREFERRED EMBODIMENTS

As regards the first conveyor line, it include a sample checking procedure to verify that the sample is in a suitable state to subject to the testing procedure(s), prior to subjecting to the testing procedure(s). For example in the case of biological samples the sample checking procedure may comprise a check on the suitability of the samples for a selected clinical test, for example a turbidity or color test to check for decomposition, contamination etc. Failure of this checking procedure may result in transfer of containers containing failed samples from the first conveyor transport lane to the accumulator lane, or alternately if the sample is still suitable for selection of other tests, instruction of the selection means to bypass the test for which the sample is not suitable. This checking procedure may be under the control of the data processing system.

In another embodiment the first conveyor line and spur line(s) may have one or more elevated sections ("alpines") to allow access for maintenance or circulation of persons through the area in which the apparatus is located. Suitably the conveyor line(s) rise to such elevated sections by means of sloping or ramped sections of the conveyor lines.

The conveyor lines may be constructed in modules, for example each module comprising a region of conveyor containing a small number, e.g. four, of sets of selection means and associated transfer means in each antiparallel section, with a local I/O control system specific to the module. Such modular construction and control has been found to be advantageous relative to a single centralized control system, in minimizing the amount of control wiring that is necessary, and facilitating maintenance.

At points on the conveyor lines where jamming of containers could occur for example where containers are transferred from one lane to another, the point may be provided with an anti-jamming mechanism, which may be of known type. For example the anti-jamming mechanism may comprise means to impart rotation to at least some of the containers about an axis perpendicular to the plane of the conveyor line. Such a mechanism may comprise holders which are rotatable about said axis, and means to contact such rotatable holders at a tangent to the axis of rotation. As such transfer points are likely to be points also where the containers are exposed to the means for reading and recording information the anti-jamming means may also comprise the rotating means which rotate the container(s) to expose the label to the means for reading information.

The spur line(s) may extend substantially at right angles from the region of the first conveyor line from which transfer of containers occurs. The combination of spur conveyor line and transfer conveyors may in such a construction be in a generally "T" shape, with the stem of the T forming the spur line, and each arm of the T being a transfer conveyor running generally parallel and alongside the first conveyor. In such a construction the spur conveyor and transfer conveyors may form an endless circulating loop, by means of the ends of the arms of the T (i.e. the ends of the transfer conveyors) being connected by a loop of the conveyor belt underneath the two arms of the T. This construction of the spur conveyor line(s) and transfer conveyors enables a particularly compact construction of the apparatus.

The invention also provides a process for subjecting samples to one or more selected test procedures at respective test stations, the process involving the use of an apparatus as described above. The process is particularly applicable to the subjecting of biological samples to clinical tests.

The sequence and physical layout of the above mentioned elements of the apparatus of the invention will be determined by determinants such as: the nature of the samples, the nature of the containers, the nature of the labels and the information thereon, the rate at which samples are to be processed in the apparatus of the invention, the number and nature of the testing procedures to which the samples are to be subjected, and the physical constraints of the site where the apparatus is to be located. Within the generality of the disclosure of the invention herein, and subject to these determinants, ways of constructing an apparatus according to this invention to meet any specific requirements will be apparent to those skilled in the art.

The apparatus of this invention will now be described by way of non limiting example only, with reference to the accompanying drawings.

DISCUSSION OF THE FIGURES

Figure 1:
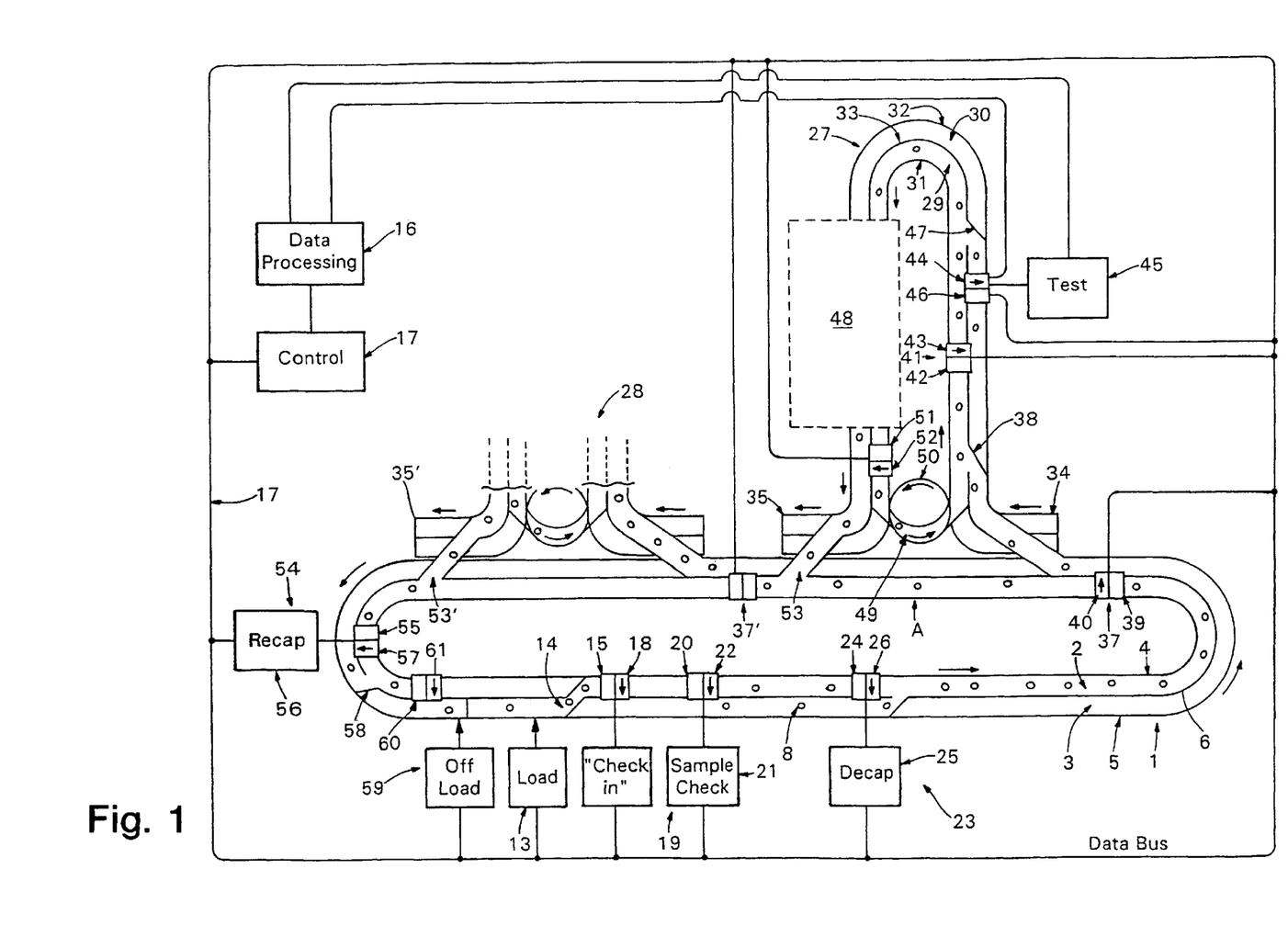
FIG. 1 shows a schematic plan diagram of the apparatus of the invention.

Referring to FIG. 1, the apparatus comprises a first counterclockwise circulating conveyor line 1 (general) having an inner lane 2 and an outer lane 3. Line 1 is a Flex-Link XM™ conveyor belt, and is set out in two substantially antiparallel moving long straight sides, turning at the ends, thereby forming a generally lozenge shape. Other geometries are possible. The outer edges of the two lanes 2, 3 are defined by respective edge walls 4, 5, and the line 1 is divided into the two lanes 2, 3 by a central dividing wall 6. The edge walls 4, 5 and the dividing wall 6 are provided with guide ridges 7 on the surfaces thereof facing lanes 2, 3.

Figure 3:
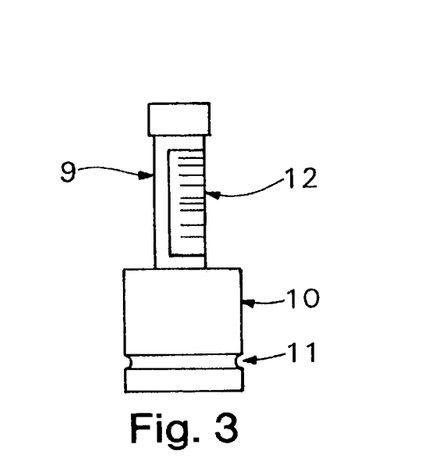
FIG. 3 shows tubes mounted in holders

Containers 8 are tubes 9 mounted in rotatable circular section holders 10, the holders having guide grooves 11 on their outer surface into which the guide ridges 7 can engage so as to guide and retain the holders on the conveyor 1, each contain a sample (not shown) of a biological material for testing. Each tube 9 is uniquely labeled with an optically readable bar code 12 which encodes information relating to the identity of the sample in the tube and the test procedures to which the sample in the tube 9 is to be subjected in the apparatus of the invention.

Containers 8 are loaded onto the outer lane 3 of conveyor 1 by a loading means 13, which comprises a generally known construction of a broad conveyor belt onto which containers 8 are placed, and are funneled to form a stream of sequential individual containers 8, which are then loaded by known means such as a stepwise rotatable wheel having circumferential receptacles for individual containers 8, and from which containers 8 may be fed out individually onto lane 3 with suitable intervals in between.

Shortly after loading onto lane 3, containers 8 are routed into inner lane 2 by a divertor 14 in the form of a set of ramp barrier. An initial means 15 for reading information from the labels, being an optical bar code reader provided with a singulator and container stopping means of generally known construction, reads information relating to the identity of each container 8 of the label, and transmits this information to a data processing system 16, via data bus 17, where it is recorded, in effect "checking in" each container 8 into the apparatus.

If a defect in a container 8 is detected by means 15, such as an unreadable or absent bar code for example, then under the control of data processing means 16 and control means 17 a divertor means 18 (the arrow drawn on the divertor means 18, and other divertor means shown indicates the direction of diversion) routes the defective container 8 onto the outer lane 3. Containers 8 which have no defects detectable at this stage being retained on the inner lane 2 of line 1. Divertor means 18 may suitably comprise a known construction of moveable barriers, for example which can be swung by compressed air actuation to close one lane and divert containers 8 to another lane. The operation of the means 15 and 18 takes optimally around 0.5 sec. in total. The inner lane 2 is consequently acting as a transport lane by which containers 8 are transported through the apparatus, and the outer lane 3 is acting as an accumulator lane into which defective containers and/or samples are routed.

After the initial reading and "checking in", samples 8 are subjected to a check procedure at 19. This check procedure at 19 comprises a means 20 for reading information from the labels, of similar construction and function to the means 15 described above and reads information relating to the identity of each container 8 and the testing procedures to which it is to be subjected, from the label. At 19 there is check equipment 21 of known type, controlled by data processing system 16 and control system 17, which applies a check of a nature appropriate to the tests to which the sample in the container 8 is to be subjected, e.g. turbidity, color etc.. If the means at 20 detects a defect in the container, in a similar manner to means 15, or if the check at 21 detects that the sample is unsuitable for a specific test, divertor means 22 similar to the means 18 route the defective container 8 into the outer, accumulator, lane 3, or alternately the data processing means 16 may record that the sample is unsuitable for the some test procedures, but suitable for others, and may subsequently cause the container 8 to bypass the testing procedure for which it is unsuitable.

At 23 is a decapping means. Means 23 comprises a means 24 for reading information from the labels, similar to means 15, which reads information relating to the identity of each container 8 and the test procedures to be applied from the label. Under the control of data processing system 16 and control system 17, if the test procedures to which the sample is to be subjected require the cap or closure of the tube 9 to be removed, a decapping device 25, which may be of known type, does so. The decapping means 23 may include divertor means 26 similar to means 18, responsive to means 24 under the control of data processing system 16 and control system 17, for routing containers 8 into the accumulator outer lane 3. The outer, accumulator, lane 3 is consequently functioning as a lane in which or from which actions can be carried out on the container 8. It will be understood that decapping means 23 may be positioned at other points in the apparatus, provided it is upstream of any test that requires a decapped container 8.

Figure 2:
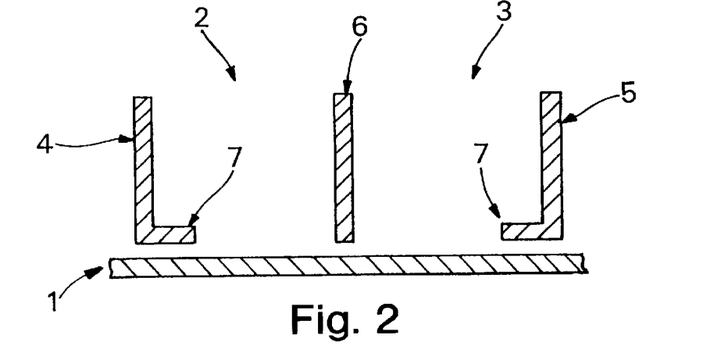
FIG. 2 shows a cross section through the conveyor line 1 of FIG. 1

The apparatus is shown with two spur conveyor lines 27 and 28, although there may be one spur line or more than two spur lines. The general construction of each spur conveyor line 27, 28 is similar to first conveyor line 1. Each spur conveyor line 27, 28 comprises an counterclockwise circulating conveyor line having an inner lane 29 and an outer lane 30. Lines 27, 28 are Flex-Link XM™ conveyor belt, and is set out in two substantially antiparallel moving long straight sides, oriented substantially at right angles to the long straight sections of line 1, having one end immediately adjacent to a the first line 1, and turning at the end remote from the first conveyor line 1. Other geometries are possible. The outer edges of the two lanes 29, 30 are defined by respective edge walls 31, 32, and the lines 27, 28 are divided into the two lanes 29, 30 by a central dividing wall 33, the central wall 33 dividing the conveyor belt 27, 28 across its width into the necessary number of lanes 29, 30. The edge walls 31, 32 and the dividing wall 33 are provided with guide ridges (not shown) on the surfaces thereof facing lanes 29, 30, the cross section being generally identical to that of the first line as shown on FIG. 2.

Figure 4:
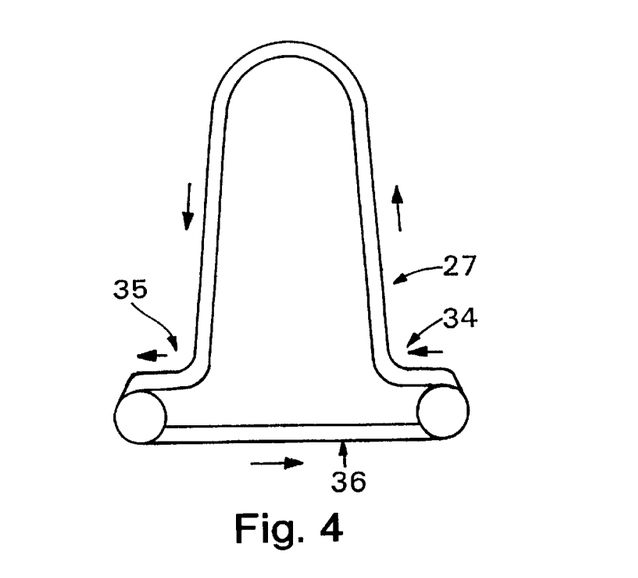
FIG. 4 shows the layout of the spur conveyor line in a perspective dismantled view.
Figure 5:
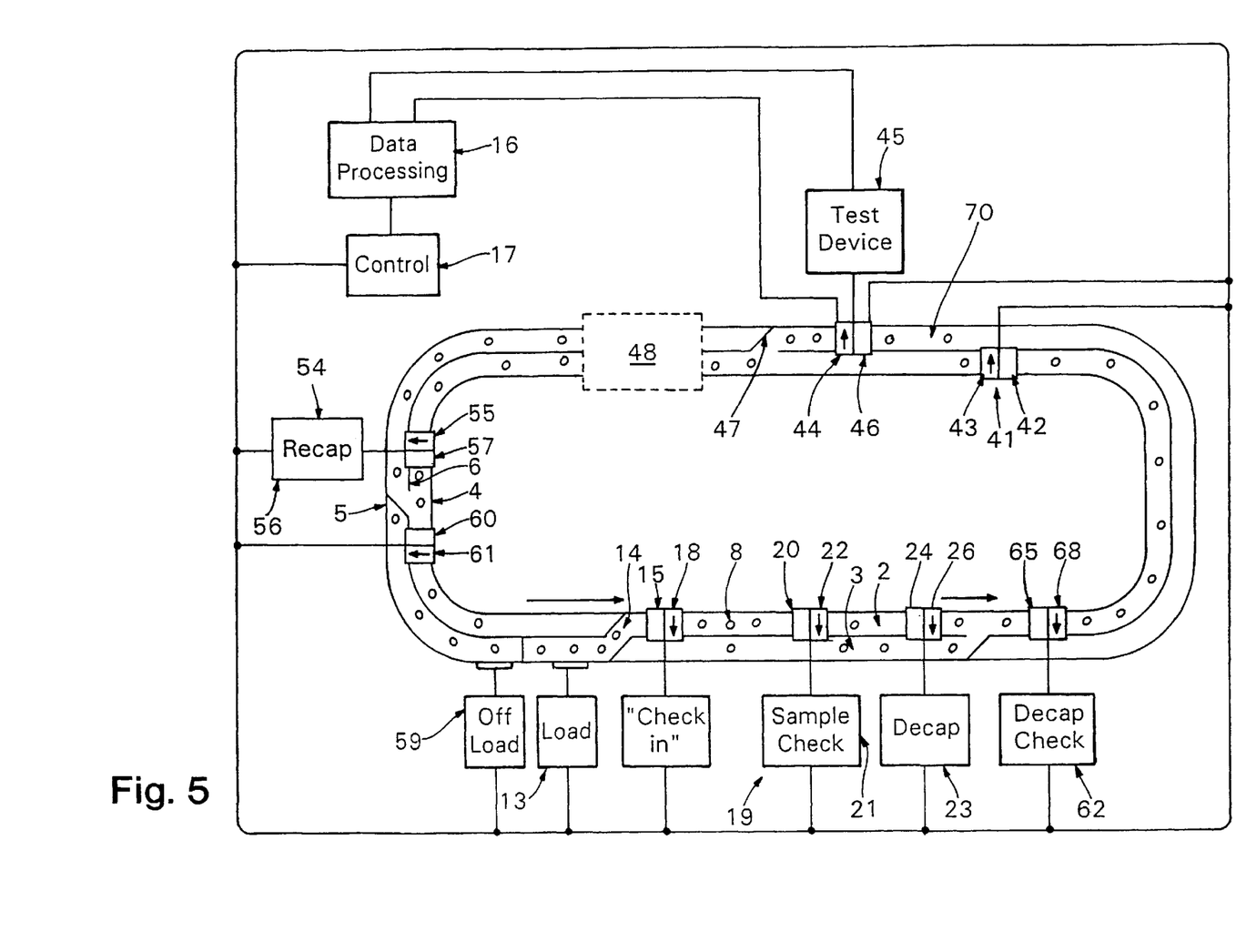
FIG. 5 shows an embodiment as preferred in FIG. 1.

At the end of the spur lines 27, 28 adjacent to line 1, spur line 27, 28 bends to form transfer lanes 34, 35 which move parallel to, alongside, and at the same speed as the outer lane 3 of the first line 1. The use of Flex-Link XM™ conveyor belt enables this. The spur line 27, 28 consequently forms substantially a "T" shape, with the sideways limbs of the T of the spur being the transfer lanes 34,35. At the ends of the transfer lanes 34, 35, the conveyor returns in a loop 36 directly underneath the limbs of the T. This is shown in a dismantled perspective view in FIG. 4, the view being looking down on the limbs of the T along the stem, i.e. in the direction of the arrow A→ in FIG. 1. The use of Flex-Link XM™ conveyor belt facilitates this, and construction in this way is found to be particularly convenient and power-efficient.

At 37 is selection means and routing means, controlled by data processing means 16 and control means 17, for selecting containers 8 and for routing selected containers 8 from the first conveyor transport lane 2 to transfer lane 34 and thence to the outer lane 29 of a selected spur line 27, from which containers 8 are shortly thereafter routed to the inner lane 29 of the spur lane 27 occurs by means of a ramp guide surface 38. The containers 8 are guided along transfer lane 34 by means of shaping the walls 5, 6 to guide the containers. Means 37 comprises a means 39 for reading information from the labels, similar to means 15, which reads information relating to the identity of each container 8 and the test procedures to be applied from the label. Under the control of data processing system 16 and control system 17, if the test procedures to which the sample is to be subjected require the container to be diverted to spur 27, a divertor means 40, similar to means 18, routes containers 8 onto the outer lane 3, and consequently onto transfer lane 34, and consequently onto outer lane 30 of spur conveyor 27. Conversely, if the test procedures to which the sample is to be subjected does not require the container to be diverted to spur 27, the divertor means 40 does not divert the container, and by default the container 8 remains on the inner, transport, lane 2 of line 1.

On spur 27 the container 8 then proceeds along the inner lane 29 of spur line 27. At 41 is selection means and transfer means, controlled by data processing means 16 and control means 17, for selecting containers 8 and for transferring selected containers 8 from the inner lane 29 of spur line 27 to the outer lane 30 of spur line 27. Means 41 comprises a means 42 for reading information from the labels, similar to means 15, which reads information relating to the identity of each container 8 and the test procedures to be applied from the label. Under the control of data processing system 16 and control system 17, if the test procedures to which the sample is to be subjected require the container to be diverted to outer lane 30, a divertor means 43, similar to means 18, routes containers 8 onto the outer lane 30. Conversely if the test procedures to which the sample is to be subjected do not require the container to be diverted to outer lane 30, or if the means 42 detects a defect in the container 8, in the manner described above, the divertor means 43 does not divert containers 8 onto the outer lane 30, so by default they remain in inner lane 29.

Outer lane 30 is a queue lane, into which containers 8 are diverted. Adjacent to lane 30 are container interface means 44 which under the control of data processing means 16 and control means 17 transfers a container 8 or a sample therein from the outer queue lane 30 to adjacent test equipment 45 controlled by data processing means 15. Data processing means 15 also records and stores the test results and associates these with the identity of the sample. The interface means 44 may be of a known type, such as the abovementioned direct sampling engine, pick and place engine, pipetting engine and batch movement engine, and the test equipment 45 may also be of a known type, for example known automated clinical test equipment. If the interface means 44 removes the container from lane 30 for the purposes of the test procedure 45, it must also return the container to lane 30. Upstream from interface means 44 may be means 46 for reading information from the labels, similar to means 14, which reads information relating to the identity of each container 8 and optionally the test procedure to be carried out, so that the test results can be associated with the identity of the sample therein, and to confirm just before testing at 45 that the test 45 is appropriate.

After completion of the test procedure at 45, and any necessary return of the container from the test procedure 45 by the interface means 44 to the outer lane 30, divertor means 47, a sloped section of wall 33, routes the container 8 back to the inner lane 29 for transport around the spur 27, inner lane 29 thus functioning as a transport lane.

Containers 8 which have at 41 not been diverted into outer lane 30 bypass the test procedure 45, and are transported further around spur 27 on inner lane 29, which functions as a transport lane.

Traveling around the spur 27 in inner transport lane 29, containers 8 may encounter a further part 48 of the spur, either simply being a conveyor line having one or more further sets of items corresponding to 41, 42, 43, 44, 45, 46, 47, which can subject the containers 8 to another test procedure. Additionally or alternatively the area 48 can subject containers 8 which have bypassed test procedure 45 to test procedures.

Although on line 27 two test procedures 45 are shown, there may be one test procedure or more than two test procedures 45. When there are two or more test procedures, 45 they may be the same test procedure or different test procedures.

At 49 the inner lane 29 is continued as a circulating lane, which may be a conveyor belt, or a turntable 50, driven by a motor (not shown). This enables containers on inner lane 27 to be recirculated on inner lane 27 of the spur 25, for example for re-testing, for example if the queue lane immediately upstream of a test procedure 45 is full (queue lane 30 between means 42 and 45 may include sensors (not shown) to detect if the lane 30 is filled, and by means of data processing means 16 and control means 17 may instruct divertor 43 not to route containers 8 into the filled queue lane 30), for example if the test procedure 45 is too busy and its capacity is exceeded. Means 51 for reading information from the labels, similar to means 15, which reads information relating to the identity of each container 8 from the label, and divertor means 52, similar to means 1 are located upstream of the point where inner lane 29 meets or merges with circulating lane 49. Under the control of data processing system 16 and control system 17, if the means 51 identifies containers 8 which are to be tested by a test procedure 45 which is busy, then divertor means 48 routes such containers 8 onto the circulating lane 46 and consequently back onto lane 30 at a point upstream of the test procedure 45 in question. Conversely, if the means 51 finds no need to circulate the containers 8, they are not routed by divertor means 48 to the circulating lane 49, and they routed along transfer lane 35 functioning as a return means to transfer containers 8 back to the inner transport lane 2 of line 1, being routed across the outer parts of conveyor 1 by a sloped part of the walls 32, 33.

Meanwhile, containers routed at 37 to bypass spur 27 flow along the inner transport lane 2 of line 1, and the flow of containers 8 along transfer lane 35 merges at 53 with the flow of containers 8 along the inner transport lane 2 of line 1.

Traveling along the inner transport lane 2 of line 1, containers 8 encounter a further means 37' duplicating the function of means 37 to select and route containers 8 onto spur 28. The construction and operation of spur 28 is in general identical to that of spur 27 and spur 28 may have additional, alternative or duplicate test procedures corresponding to test procedures 45 of spur 27. Consequently spur 28 is not drawn or described herein in detail, as its features correspond mutatis mutandis to spur 27. Containers 8 are transferred by transfer lane 35' back onto the inner transport lane 2 of line 1 in a manner analogous to spur 27, the flow of containers 8 merging at 53'.

On the inner transport lane 2 of line 1 downstream of 53' is located a recapping means 50. Means 54 may be located anywhere on line 1 or on spur 27 or 28 where containers 8 are downstream of test procedures 45 which require uncapped containers 8 for the test procedure 45 to be carried out. Means 54 comprises means 55 for reading information from the labels, similar to means 15, which reads information relating to the identity of each container 8 from the label. Under the control of data processing means 16 and control system 17, means 55 determines whether the container 8 has been subjected to a decapping procedure at 23, and if it has and requires a cap to be re-applied, a cap is applied to the container 8 by a capping device 56, which may be of known type. A divertor means 57 similar to means 18 routes the container 8 into outer, accumulator lane 3 where the recapping operation can be carried out, and then ramped guide 58 routes the container 8 back onto transport lane 2.

On the first conveyor line 1 downstream of the spurs 27, 28 and recapper 54 is an off-loading means 59, which comprises means 60 for reading information from the labels, similar to means 15, which reads information relating to the identity of each container 8 from the label, and a divertor means 61 similar to means 18 to divert containers 8 off the inner transport lane 2 of line 1 and off line 1 altogether. The off loading means 59, under the control of the data processing means 16 and control system 17, responding to information read by means 60, deposits off-loaded containers 8 into known locations (not shown), for example in stacked trays, of which the XYZ coordinates of each container are recorded by the data processing system, and may be accessed if necessary subsequently. The reading of the information by means 60, and recording by data processing system 16 identifies that the container 8 has left the conveyor 1, in effect "checking out" the container 8 from the apparatus.

The means 15 and corresponding means for reading information from the label on the containers allow repetitive confirmation of the identity and position of the tube in the apparatus, and at each of these means defects can be detected, and defective containers can be diverted from transport lanes to accumulator lanes. This provides for accuracy and reliability in the apparatus, and a rapid identification of problems or faults in the apparatus.

Although test procedures 45 are described above as automated test equipment, they may alternatively be test stations where containers are off loaded by means analogous to 59 for manual tests, such as long term incubations.

Although line 1 is described as having one accumulator lane 3, it could alternatively have two or more accumulator lanes, which may for example be further lanes parallel to those 2, 3 shown, or may alternatively be elevated above the line 1, for example linked to lanes 2, 3 by ramped sections of conveyor belt.

Also sections of both lanes 2, 3 of line 1 may be elevated, for example to provide an access bridge between spurs 27, 28, and such elevated sections may be elevated by means of such ramped sections of conveyor belt.

The first line 1 and the spur lines 27, 28 may each be driven by respective motors, such as electric motors having speed controls, but the use of the abovementioned Flex-Link XM™ series conveyor enables a first conveyor line 1 and at least one spur line to be driven by a single motor.

At points such as 53, 53' and other points where a divertor means causes containers 8 to join another lane, there may be antijamming devices (not shown) to prevent jamming at the junction, suitably by causing the samples 8 to rotate and thereby roll apart from each other.

In operation, when first conveyor 1 and spur conveyors 27, 28 are Flex-Link XM™ series conveyor, they can conveniently be driven at 10–50 fpm, for example being adjustable to set speeds from 10 fpm to 30 fpm, or modifiable to provide set speeds of 20–50 fpm. Such speeds enable the apparatus to throughput samples of biological materials in tubes at a rate of ca. 5000 samples per hour.

The spurs 27, 28 and line 1 may be of modular construction, such that short lengths of the line, including a small number of means controlled by control system 17, may be controlled as a unit. This modular construction minimizes the amount of interconnective wiring that is necessary.

What is claimed is:

1. An automated conveyor system for transporting biological specimens contained in uniquely identified containers to one or more selectable stations, said conveyor system comprising:

(a) a plurality of independently moveable holders, each capable of holding one of said biological specimen containers;

(b) a conveyor comprising:

(1) a single conveyor belt for supporting and moving said holders, said conveyor belt having at least two lanes, and (2) at least one gate for routing said holders between lanes;

(c) at least one reader positioned in relationship to said belt in a manner that allows for reading the unique identifier of each container when the container is in its holder;

(d) at least one electronic data processor for receiving data from said reader and associating the unique identifier data with another data file containing information defining at least one test to be performed on the specimen in that container, which, in combination, controls the movement of said container through said system;

(e) at least one station for acting on said containers, interfaced with at least one lane of said conveyor, and operating under the direct or indirect control of said electronic data processor.

2. An apparatus according to claim 1 which is circulating in design and has:

a continuous conveyor belt;

one inner lane and one outer lane with at least one gate system for routing holders between the lanes, one lane being a transport lane one lane being an accumulator lane; and the outer edges of the lanes being defined by edge walls and the single belt being divided into two lanes by a central dividing wall.

3. An apparatus according to claim 1 which is linear and has a continuous conveyor belt;

at least one gate system for routing holders between the lanes, one lane being an accumulator lane and the other being lane being a transport lane; and the outer edges of the lanes being defined by edge walls and the single belt being divided into two lanes by a central dividing wall.

4. The apparatus of claim 1, 2 or 3 wherein at least one wall defining each lane has at least one guide ridge on the surface facing the lane it defines; and said holders having at least one guide groove which engages the guide ridge in said wall.

5. The apparatus of claim 1, 2 or 3 wherein a lane is a transport lane at one point in the operation of the system and an accumulator lane at another point in the operation of the system, or an accumulator lane at one point in the operation and a transport lane at another point.

6. The apparatus of claim 1 or 2 where the inner lane is the transport lane and the outer lane is the accumulator lane.

7. The apparatus of claim 1 which has a detector which detects the integrity of the container and/or the presence or absence of a unique label.

8. The apparatus of claim 1 which has a device to stop and isolate at least one holder.

9. The apparatus of claim 1, 2 or 3 further comprising a device positioned for removing the closure on a container while the container is in its holder.

10. The apparatus of claim 1, 2 or 3 which has a gate in the form of a ramp barrier for routing holders between said lanes.

11. The apparatus of claim 1, 2 or 3 which has an active gate for routing holders between lanes.

12. The apparatus of claim 1, 2 or 3 further comprising an area along said belt for loading holders with or without containers onto one of said lanes or for loading containers into holders on a lane.

13. The apparatus of claim 1 further comprising a station which is a mechanical device under control of the, or a, data processor for removing containers from holders in an accumulator lane or for removing holders and containers from said lane.

14. The apparatus of claim 1 or 13 having a rack located adjacent to or integrated into said station for receiving and holding a plurality of containers, wherein said mechanical device places said container in said rack after removing said container from said holder, or removes containers from said rack and places them in holders on the system.

15. An automated conveyor system for transporting biological specimens contained in uniquely identified containers said conveyor system comprising;

a first conveyor line for transporting samples containing in uniquely labeled containers, said line have at least two lanes with means for routing containers between said lanes, at least one lane being a transport lane and at least one other lane being and accumulator lane, loading means for loading said containers onto the apparatus, electronics means for reading and recording the unique label information from said labels of containers, data processing means for electronically recording, storing and processing said information, electronic control means for routing and tracking said samples in response to said recording information, at least one interface means for routing containers from the first conveyor line to a spur conveyor line, one or more spur conveyor lines for transporting said containers to one or more selectable test stations, said spur line(s) having at least two lanes, with means for routing containers between said lanes, at least one of said lanes being a transport lane and at least one of said lanes being a queue lane, and having a container interface device and a sample testing procedure located adjacent to said spur line(s);

selection means and routing means, controlled by said data processing means, for selecting containers for routing by the interface device from the first conveyor transport lane to the transport lane of a selected spur line, selection means and routing means, controlled by said data processing means, for selecting containers and for routing selected containers from the spur transport lane to the queue lane adjacent to a selected test station;

a container interface device for presenting a container or sample from the container to a test procedure and capable of interacting with a container in the queue lane and the staging area of a test procedure;

test means for carrying out the test procedure;

means to record and store the results of the said test procedure;

means to route container from the queue lane to the spur line transport lane;

at least one interface means for routing containers from the spur conveyor line to the first conveyor line;

off-loading means to off-load containers from the apparatus.

* * * * *